United States Patent
Scheidel et al.

(10) Patent No.: US 7,612,224 B2
(45) Date of Patent: Nov. 3, 2009

(54) ISOMERISATION OF CIS-2-PENTENENITRILE TO FORM 3-PENTENENITRILE IN A REACTIVE DISTILLATION

(75) Inventors: Jens Scheidel, Hirschberg (DE); Tim Jungkamp, Kapellen (BE); Michael Bartsch, Neustadt (DE); Gerd Haderlein, Grünstadt (DE); Robert Baumann, Mannheim (DE); Hermann Luyken, Ludwigshafen (DE)

(73) Assignee: BASF Aktiengesellschaft (DE)

( * ) Notice: Subject to any disclaimer, the term of this patent is extended or adjusted under 35 U.S.C. 154(b) by 555 days.

(21) Appl. No.: 10/585,626

(22) PCT Filed: Jan. 27, 2005

(86) PCT No.: PCT/EP2005/000782

§ 371 (c)(1),
(2), (4) Date: Jul. 11, 2006

(87) PCT Pub. No.: WO2005/073177

PCT Pub. Date: Aug. 11, 2005

(65) Prior Publication Data

US 2007/0287851 A1    Dec. 13, 2007

(30) Foreign Application Priority Data

Jan. 29, 2004    (DE) .................. 10 2004 004 716

(51) Int. Cl.
*C07C 291/00* (2006.01)
(52) U.S. Cl. ...................................... 558/355
(58) Field of Classification Search .................. 558/355
See application file for complete search history.

(56) References Cited

U.S. PATENT DOCUMENTS 3,526,654 A     9/1970  Hildebrand

FOREIGN PATENT DOCUMENTS

| DE | 103 23 803.4 | 4/2003 |
| WO | WO-02/081417 | 10/2002 |
| WO | WO-2004/094364 | 11/2004 |

*Primary Examiner*—Kamal A Saeed

(57) ABSTRACT

A process is described for isomerizing pentenenitrile in a reactant stream, wherein the isomerization is effected over a heterogeneous catalyst in a distillation column in such a way that, during the isomerization of the isomerization reactant, it is distillatively depleted in relation to the isomerization product in the reaction column of the distillation column.

12 Claims, 1 Drawing Sheet

ISOMERISATION OF CIS-2-PENTENENITRILE TO FORM 3-PENTENENITRILE IN A REACTIVE DISTILLATION

RELATED APPLICATIONS

This application is a national stage application (under 35 U.S.C. 371) of PCT/EP2005/000782 filed Jan. 27, 2005, which claims benefit to German application 10 2004 004 716.2 filed Jan. 29, 2004.

DESCRIPTION

The present invention relates to a process for isomerizing pentenenitrile in a reactant stream.

Adiponitrile is an important starting material in nylon production and is obtained by double hydrocyanation of 1,3-butadiene. In the first hydrocyanation, the 1,3-butadiene is hydrocyanated to 3-pentenenitrile, in the course of which the by-products obtained are mainly cis-2-pentenenitrile, 2-methyl-2-butenenitrile, 2-methyl-3-butenenitrile, $C_9$ nitriles and methylglutaronitrile. In a second, subsequent hydrocyanation, 3-pentenenitrile is reacted with hydrogen cyanide to give adiponitrile. Both hydrocyanations are catalyzed by nickel (0)-phosphorus complexes. Unlike 3-pentenenitrile, for example trans-3-pentenenitrile, the cis-2-pentenenitrile cannot be hydrocyanated to adiponitrile in the presence of nickel (0)-containing catalysts. This reduces the yield of the adiponitrile synthesis.

It is accordingly desirable to isomerize cis-2-pentenenitrile to trans-3-pentenenitrile, in order then to be able to recycle it back into the adiponitrile synthesis.

U.S. Pat. No. 3,526,654 discloses the isomerization of cis-2-pentenenitrile to trans-3-pentenenitrile in the presence of silicon dioxide, alumina or sodium-calcium silicate, the catalysts being present in various modifications. The isomerization is carried out in the liquid or gas phase at temperatures of from 25° C. to 500° C. Owing to a low conversion and a longer isomerization time, this process is uneconomic. In general, the rate of an isomerization can be raised by an increase in the reaction temperature. However, this is not appropriate to the purpose in the present isomerization of cis-2-pentenenitrile to trans-3-pentenenitrile, since, in the case of pentenenitriles, an increase in the reaction temperature within the temperature range disclosed in U.S. Pat. No. 3,526,654 leads to formation of an industrially unacceptable high amount of oligomers and polymers.

DE-A-103 23 803 describes the isomerization of cis-2-pentenenitrile to 3-pentenenitrile over alumina as a catalyst. In this isomerization, yields of 30% based on cis-2-pentenenitrile are generally achieved. When the conversion of cis-2-pentenenitrile is increased, the result is increased formation of trans-2-pentenenitrile relative to the desired formation of trans-3-pentenenitrile.

It is thus an object of the present invention to provide a process which enables the isomerization, especially of cis-2-pentenenitrile to trans-3-pentenenitrile, with conversions based on the isomerization reactant which are economically acceptable.

At the same time, a high space-time yield of trans-3-pentenenitrile based on cis-2-pentenenitrile should be achieved.

The object of the present invention is achieved by a process for isomerizing pentenenitriles in a reactant stream.

DETAILED DESCRIPTION

Figure 1:
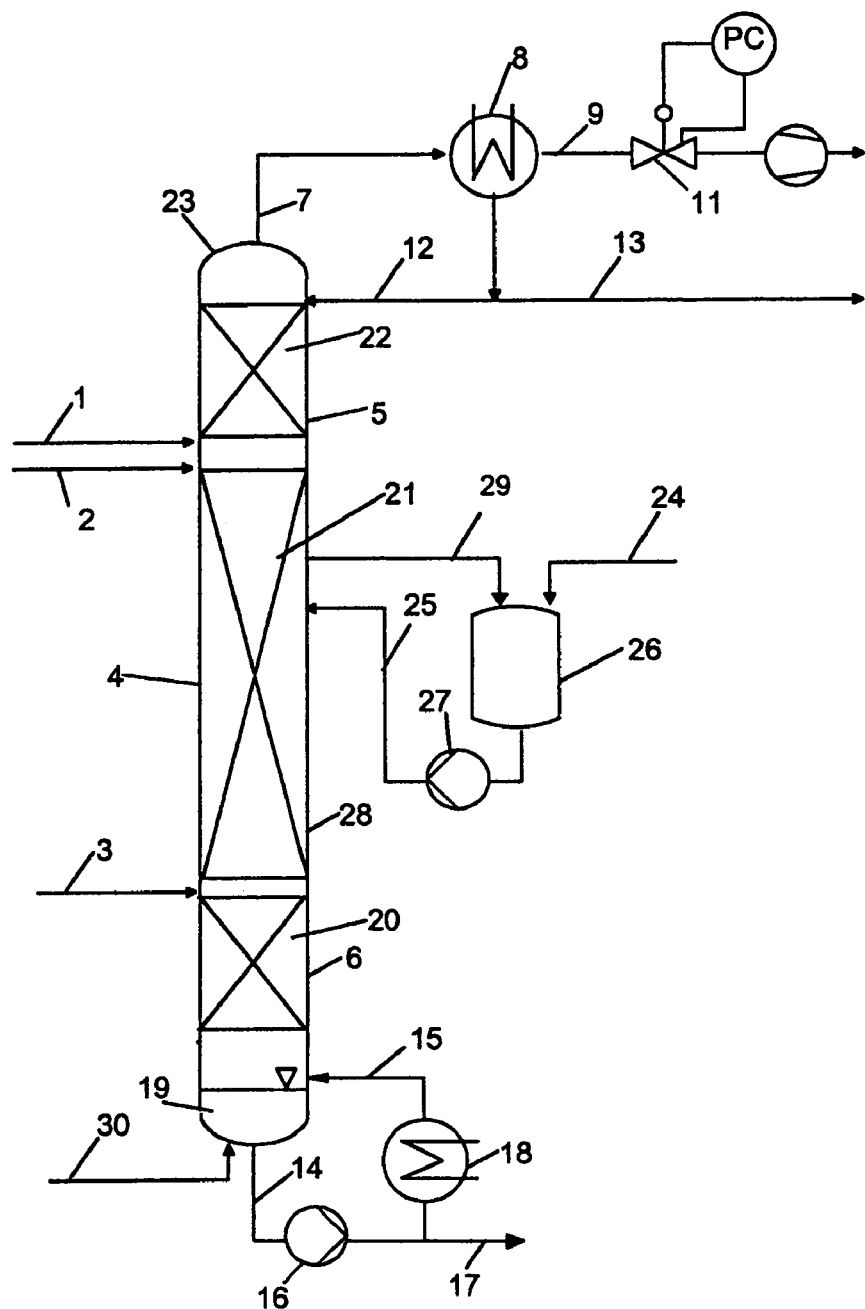
FIG. 1 schematically shows one arrangement for carrying out the process of this invention.

In the process according to the invention, the isomerization takes place over at least one heterogeneous catalyst in a distillation column at least comprising a bottom zone, a reaction zone and a top zone, and, during the isomerization, the isomerization reactant is distillatively enriched in the reaction zone of the distillation column in relation to the isomerization product. It is not ruled out that isomerization also takes place in the top or bottom zone.

In a preferred embodiment of the present invention, cis-2-pentenenitrile is isomerized to trans-3-pentenenitrile.

In an isomerization of cis-2-pentenenitrile, the reactant stream may comprise further constituents which are in particular selected from the group consisting of C5-mononitriles, C6-dinitriles, aliphatic C1- to C16-alkanes, cyclic C1- to C16-alkanes, aliphatic C1- to C16-alkenes, cyclic C1- to C16-alkenes, more preferably starting from a group consisting of trans-3-pentenenitrile, trans-2-pentenenitrile, cis-3-pentenenitrile, 4-pentenenitrile, Z-2-methyl-2-butenenitrile, E-2-methyl-2-butenenitrile, 2-methyl-3-butenenitrile, methylglutaronitrile, ethylsuccinonitrile, adiponitrile, valeronitrile, cyclohexane, methylcyclohexane, n-heptane, n-octane, vinylcyclohexane, ethylidenecyclohexene and vinylcyclohexene.

The reactant stream preferably starts from a process for hydrocyanating 3-pentenenitrile.

The content of cis-2-pentenenitrile in the reactant stream is preferably from 0.5 to 100% by weight, more preferably from 1.0 to 98% by weight, in particular from 1.5 to 97% by weight.

The reactant stream used in the process according to the invention, which comprises cis-2-pentenenitrile, is generally obtained in processes known per se. An example thereof is a process for hydrocyanating 3-pentenenitrile, 3-pentenenitrile referring to trans-3-pentenenitrile, cis-3-pentenenitrile, mixtures thereof or a mixture comprising cis- or trans-3-pentenenitrile. Alternatively, the reactant stream may also stem from a hydrocyanation of 4-pentenenitrile or mixtures comprising 4-pentenenitrile to adiponitrile.

In a preferred embodiment, the process according to the invention may be integrated into a hydrocyanation process for preparing adiponitrile.

The process according to the invention is preferably carried out in a distillation column at least comprising a bottom zone, a reaction zone and a top zone. Bottom zone, reaction zone and top zone are arranged in the sequence given above from bottom to top in the distillation column. It is not ruled out that reaction may also take place in the bottom or top zone.

Additionally, the distillation column may comprise internals having distillative separating action. These additional internals are preferably disposed below and/or above the reaction zone. In the lower separating zone, i.e. the separating zone below the reaction zone, a high-boiling isomerization product is substantially removed from low-boiling components. For example, trans-2-pentenenitrile and trans-3-pentenenitrile are separated from unconverted cis-2-pentenenitrile. In the upper separating zone, i.e. the separating zone above the reaction zone, low-boiling secondary components are substantially removed from high-boiling components. Here, for example, any E-2-methyl-2-butenenitrile introduced with the reactant stream is separated from trans-3-pentenenitrile and trans-2-pentenenitrile. Equally, it is possible to deplete trans-3-pentenenitrile and trans-2-pentenenitrile from unisomerized cis-2-pentenenitrile. These separations are only listed by way of example and are not restrictive.

In the event of optimal column configuration, all of the cis-2-pentenenitrile of the reactant stream may thus be converted without an additional reactor and all of the trans-3-pentenenitrile obtained in the bottom without an additional separating apparatus. The additional internals having distillative separating action (separating zones) are generally advantageous, but not necessarily required. One or both of the two separating zones may thus also be dispensed with.

The reaction zone consists generally of a plurality of different subregions having different functions. The subregions differ by the task of transporting gas to the top of the column and the task of drawing off liquid in the direction of the column bottom. In addition, liquid distributors within the reaction zone may be needed to ensure optimal distribution of liquid over the column cross section. The internals for introducing heat into the column may also be disposed in the reaction zone. In addition, solids suitable as a catalyst are preferably inserted into the part which conducts predominantly liquid, as described hereinbelow.

The isomerization of cis-2-pentenenitrile to trans-3-pentenenitrile is carried out over a heterogeneous catalyst.

The isomerization is effected substantially on the column internals of the reaction zone or over the solid which is suitable as a heterogeneous catalyst for the purposes of the process according to the invention and has been introduced into interstices of these internals. The resulting products, preferably trans-3-pentenenitrile, cis-3-pentenenitrile and trans-2-pentenenitrile, are preferably removed simultaneously. The dimension of the reaction zone depends upon the desired degree of conversion and the amount of cis-2-pentenenitrile in the reactant stream.

The catalyst may be mounted in the reaction zone on trays having high residence time of the liquid, for example valve trays, preferably bubble-cap trays or related designs, for example tunnel-cap trays or Thormann trays, or be installed in the reaction zone as a catalyst bed. However, it is also possible to use structured packings containing catalyst, for example Montz MULTIPAK or Sulzer KATAPAK, or to introduce the catalyst into the column in the form of random packings. Moreover, it is possible to use catalytically active distillation packings or catalyst-filled fabric bags, known as bales or Texas teabags.

A preferred embodiment is the use of structured catalyst packings or random packings, into which the catalyst particles are inserted loosely under the action of gravity and distributed, and are discharged again if required. Particular preference is given to using a structured catalyst packing or random packings which have first and second subregions, the catalyst particles being inserted loosely into the first subregions of the structured packing under the action of gravity, distributed, and discharged again if required, but no catalyst particles being insertable into the second subregions owing to the geometric circumstances in comparison to the catalyst particles. This is ensured by the quotient of the hydraulic diameter for the gas stream through the structured packing or random packing and the equivalent diameter of the catalyst particles in the first subregions being preferably in the range from 2 to 20, more preferably in the range from 5 to 10, the catalyst particles being loosely inserted into the interstices under the action of gravity, distributed, and discharged if required, and by the quotient of the hydraulic diameter for the gas stream through the structured packing or the random packings and the equivalent diameter of the catalyst particles in the second subregions being less than 1, and by no catalyst particles being inserted into the second subregions. The hydraulic diameter for the gas stream through the packing is calculated from four times the area flowed through divided by the circumference of the gas channels of the structured packing. The equivalent particle diameter is calculated from six times the volume of the particle divided by the surface area of the particle (on this subject, cf. VDI Wärmeatlas, 5th edition, 1988 Lk1). This structured catalyst packing is described in the patent application WO 03/047747 A1, and the structured catalyst packing described there is incorporated by reference into the present application. The above-described structured catalyst packing is particularly advantageous when the process according to the invention is carried out in the liquid phase.

In the separating zones of the distillation column, internals having distillative separating action are used. Preference is given here to using column internals having a high number of separating stages, such as metal fabric packings or sheet metal packings having ordered structure, for example Sulzer MELAPAK, Sulzer BX, Montz B1 types or Montz A3 types.

To carry out the process according to the invention, preference is given to using distillation columns which have as, including the reaction and separating zones, from 10 to 100 trays, more preferably from 10 to 60 trays. It has been found to be particularly advantageous when the separating zone above the reaction zone has from 0 to 50 trays, preferably from 2 to 40 trays. It has been found to be particularly advantageous when the reaction zone has from 0 to 100 trays, preferably from 2 to 40 trays. It has been found to be particularly advantageous when the lower separating zone has from 0 to 50 trays, preferably from 5 to 30 trays. The same applies to what are known as theoretical plates in the case of other column internals.

The process according to the invention for isomerizing cis-2-pentenenitrile is preferably carried out in such a way that the cis-2-pentenenitrile to be isomerized or a mixture comprising it is metered via one or more feeds which, depending upon the mixture composition, may be below, within or above the reaction zone.

The feed of the reactant stream may also be in the region of the internals which only have distillative separating action but no catalytic activity. The feed of the reactant stream may be either in the upper or in the lower separating zone. It is likewise possible to meter in reactant streams via different feeds within the same or different separating zones and/or the reactant zone.

In the distillation column, pressure and temperature are preferably adjusted in such a way that high reaction rates result at sufficiently high selectivity. The pressure in the top zone is preferably adjusted in such a way that the temperature in the bottom zone is between 30 and 300° C., preferably between 40 and 250° C., in particular between 50 and 200° C. The residence time in the distillation column is preferably from 1 minute to 10 hours, more preferably from 12 minutes to 3 hours.

The optimal temperature and pressure conditions are determined generally by the insertion of the isomerization into a process, for example the double hydrocyanation of 1,3-butadiene to adiponitrile, and the working temperature of the catalyst. The temperature may be adjusted using a vacuum pump and/or a pressure regulation device, so that the pressure conditions are matched to the demands of the process.

When heterogeneous catalysts are used, the isomerization takes place in the region of the reaction zone of the distillation column. The superimposed distillation continuously withdraws the reaction products formed from the reaction equilibrium and thus from the reaction zone, and they then reach the bottom of the distillation column and are preferably drawn off via a stream. The superimposed distillation thus ensures a positive influence of the reaction equilibrium in the sense that the pentenenitrile to be isomerized is always enriched in the region of the reaction zone and the isomerized pentenenitrile and other higher-boiling isomerization products or by-products in comparison to the pentenenitrile to be isomerized are depleted in the reaction zone. This ensures high yields of isomerized pentenenitrile with respect to the pentenenitrile to be isomerized.

The higher-boiling isomerization product collects in the bottom zone of the distillation column and may be drawn off there via a bottom stream, for example by means of a pump, if appropriate together with any by-products of the isomerization having a higher boiling point than the pentenenitrile to be isomerized, and also, if appropriate, components having a higher boiling point that the pentenenitrile to be isomerized which are already in the reactant stream. In a preferred embodiment of the present invention, a portion of the bottom stream is evaporated using an evaporator and recycled into the distillation column via a vapor line. This generates the vapors required for the distillation.

It is also possible to remove low-boiling components by additionally feeding an inert gas into the bottom zone of the distillation column. Examples of suitable inert gases are nitrogen or noble gases, such as argon or helium, or mixtures thereof or mixtures comprising this gas.

At the top of the column accumulate unconverted pentenenitrile to be isomerized and any components from the reactant stream having a lower boiling point than the pentenenitrile to be isomerized, if appropriate together with low-boiling by-products of the isomerization. In a preferred embodiment of the present invention, this top stream is conducted via a line into a condenser, condensed and discharged via a further line. Preference is given to introducing a portion of the condensate back into the distillation column as reflux. In a preferred embodiment, the amount of the portion of the condensate which is introduced back to the column is more than 50% of the condensate, preferably more than 90% of the condensate. In this way, the internal reflux in the column allows an advantageous concentration profile to be attained.

Preference is given to adjusting the concentration profile in the column by the energy input and the reflux ratio in such a way that an accumulation of the pentenenitrile to be isomerized forms at the upper end of the reaction zone compares to the lower end of the reaction zone. A high concentration of the low-boiling reactants may thus be attained in the reaction zone, which leads to high selectivities for the trans-3-pentenenitrile isomerization product which is favored kinetically at low local conversions.

A reflux ratio between 1 and 3000, more preferably between 2 and 500, based on the feed rate, should preferably be established.

To increase the residence time in the reaction zone, it is possible to pass a substream through one or more side draws out of the distillation column through one or more vessels and to recycle the substreams leaving these vessels back into the column with the aid of a pump in each case. The vessels may be charged with heterogeneous catalyst. In a preferred embodiment, the vessels are heated. The temperature in the vessels should preferably correspond to the temperature of the liquid phase at the draw tray.

It has also been found to be advantageous when heat is supplied to the distillation system consisting of the distillation column and, if appropriate, the vessel or vessels not only via the evaporator, but also additionally via external heat exchangers or via heat exchangers disposed directly on the column internals.

It is additionally possible to draw off substreams via side draws from any points in the column. For example, it is also possible to operate the column under total reflux and discharge intermediate boilers within the boiling range between the pentenenitrile to be isomerized and the isomerized pentenenitrile via a side draw below the catalyst packing but above the feed.

The process according to the invention is carried out in the presence of at least one heterogeneous catalyst. In addition, it is also possible to carry out the isomerization in the presence of at least one heterogeneous catalyst with addition of at least one homogeneous catalyst.

The heterogeneous catalyst used is, for example an oxide of transition group 3 or 4 or of main group 3 or 4 of the Periodic Table of the Elements.

According to the invention, the isomerization is preferably carried out in the presence of alumina as a heterogeneous catalyst, the alumina having a BET surface area of preferably at least 50 m$^2$/g, more preferably at least 70 m$^2$/g, in particular at least 100 m$^2$/g. The alumina should preferably have a BET surface area of at most 400 m$^2$/g, more preferably at most 350 m$^2$/g, in particular at most 300 m$^2$/g.

In the context of the present invention, the BET surface area refers to the specific surface area which is determined by measuring the amount of gas physisorbed by the method described in Brunauer, Emmett, Teller, J. Am. Chem. Soc. 60 (1938), page 309.

The alumina may, if appropriate, be present in pure form.

However, it is also possible to use alumina which includes further compounds, for example rare earth oxides such as cerium oxide, praseodymium oxide, silicon dioxide, titanium dioxide, iron oxide, alkali metal oxides, alkaline earth metal oxides or mixtures thereof. Such compounds may be present preferably in amounts of from 10 ppm by weight to 10% by weight, more preferably from 500 ppm by weight to 7% by weight, in particular from 0.1% by weight to 5% by weight, based on the sum of alumina and such compounds. In addition, further anions such as hydroxide ions may be present in addition to the oxide anion.

If, in addition to the heterogeneous catalyst, a homogeneous catalyst is also used in the process according to the invention, the latter is a which is selected from the group of the C1- to C20-mono- and -diamines, preferably the C4- to C9-diamines, more preferably hexylamine. In addition, any homogeneous catalyst to be used may be an ionic liquid which is selected from the group consisting of Brønsted acid adducts of organic nitrogen-containing substances.

In the process according to the invention, in addition to the at least one heterogeneous catalyst, a plurality of homogeneous catalysts may also be used.

In a particularly preferred embodiment, the process according to the invention for isomerization may be integrated into an overall process, in which a) 3-pentenenitrile or a mixture comprising 3-pentenenitrile is hydrocyanated to adiponitrile in the presence of a nickel(0)-containing catalyst by processes known per se while obtaining cis-2-pentenenitrile as a by-product, b) cis-2-pentenenitrile is removed fully or partly from the product mixture, if appropriate together with other substances from the hydrocyanation, for example by distillation, c) cis-2-pentenenitrile from step b) is isomerized by the above-described process according to the invention to obtain a bottom stream comprising trans-3-pentenenitrile, with or without further compounds which are selected from the group consisting of trans-2-pentenenitrile, 4-pentenenitrile and cis-3-pentenenitrile, and a top stream comprising nonisomerized cis-2-pentenenitrile and any compounds having a lower boiling point than trans-3-pentenenitrile and which are selected from the group consisting of C5-nitriles, for example Z-2-methyl-2-butenenitrile, E-2-methyl-2-butenenitrile, 2-methyl-3-butenenitrile, valeronitrile and other components stemming from the hydrocyanation and having a lower boiling point than trans-3-pentenenitrile, d) any cis-2-pentenenitrile present is removed from the bottom stream obtained in step c), for example by distillation, and recycled into step c) while obtaining a residual stream, e) the residual stream obtained in step d) is recycled into step a).

The bottom stream from c) may contain a residual proportion of cis-2-pentenenitrile. This proportion is preferably less than 10% by weight, more preferably less than 1% by weight, based on the bottom stream.

The top stream from c) may contain a residual proportion of trans-3-pentenenitrile. This proportion is preferably less than 10% by weight, more preferably less than 5% by weight, based on the top stream.

In step a), the nickel(0)-containing catalyst used may preferably be one which, in addition to nickel(0), also has a monovalent or a polyvalent ligand or a mixture of monovalent and polyvalent ligands, more preferably a monovalent ligand and a chelate ligand, especially preferably a chelate ligand which has a plurality of, such as two or three, trivalent phosphorus atoms capable of bonding to the said nickel(0), each of which may be present independently as a phosphine, phosphinite, phosphonite or phosphite. Particularly advantageously, the catalyst should also contain a Lewis acid. Such catalyst systems are known per se.

One means of increasing the conversion is the removal of the reaction product of the isomerization, in order thus to shift the equilibrium to the side of the desired isomerized pentenenitrile. One means of removing the isomerized pentenenitrile from the equilibrium is to utilize the higher boiling point of the isomerized pentenenitrile in comparison to the pentenenitrile to be isomerized.

A particularly preferred version of the process according to the invention is described hereinbelow for the isomerization of cis-2-pentenenitrile to trans-3-pentenenitrile over a heterogeneous catalyst with reference to FIG. 1:

The process according to the invention is carried out in such a way that cis-2-pentenenitrile or a mixture comprising it is metered via feeds 1, 2 or 3, below, within or above the catalyst-containing region 21, to a distillation column 4 functioning as a reaction column.

The pressure and temperature are adjusted in such a way that high reaction rates result at sufficiently high selectivity. The pressure on the gas side 9 downstream of the top condenser is preferably adjusted in such a way that the temperature in the bottom 19 is between 30° C. and 300° C. The pressure can be adjusted with a vacuum pump 10 and/or a pressure regulating device 11. FIG. 1 shows the design with a pressure regulating device 11. In its place, for example, the vacuum pump 10 may be installed.

Over the catalyst in the region of the internals 21 of the reaction column 4, the isomerization of cis-2-pentenenitrile takes place. The superimposed distillation continuously withdraws the reaction products formed from the reaction equilibrium and the reaction zone and they reach the bottom 19 of the distillation column and are drawn off via stream 14. The superimposed distillation ensures a positive influence of the reaction equilibrium in the sense that cis-2-pentenenitrile always accumulates in the region of the reaction zone 21, and trans-3-pentenenitrile and other reaction products having a higher boiling point than cis-2-pentenenitrile are depleted in the reaction zone and thus ensure high yields of trans-3-pentenenitrile based on the cis-2-pentenenitrile used.

The higher-boiling reaction product collects in the bottom 19 of the distillation column 4 and is drawn off via the bottom stream 14 by means of a pump 16, if appropriate together with by-products of the isomerization having a higher boiling point than cis-2-pentenenitrile, and also components having a higher boiling point than cis-2-pentenenitrile which are already present in the reactant stream. A portion of the bottom stream 14 is evaporated using an evaporator 18 and conducted into the column via the vapor line 15; the other portion 17 is discharged. To withdraw low-boiling components, an inert gas 30 is initially fed into the bottom of the column.

At the top 23 of the column 4 accumulate unconverted cis-2-pentenenitrile and any components from the reactant stream having a lower boiling point than cis-2-pentenenitrile, if appropriate together with low-boiling by-products of the reaction. This is conducted via line 7 into the condenser 8, condensed and discharged via line 13. A portion of the condensate is introduced back to the column as reflux 12.

This accounts for preferably more than 30%, more preferably for more than 90%, of the condensate. In this way, the internal reflux in the column allows an advantageous concentration profile to be attained.

Preference is given to adjusting the concentration profile in the column by the input of energy and the reflux ratio in such a way that an accumulation of cis-2-pentenenitrile forms at the upper end of the reaction region 21 compared to the lower end of the reaction region. A high concentration of the low-boiling reactant may thus be attained in the reaction region, which leads to high selectivities for the trans-3-pentenenitrile reaction product favored kinetically at low local conversions. A reflux ratio between 2 and 500 is attained.

On the column internals of the reaction zone 21 above the feed point 3 of the column 4, the reactant stream is substantially converted with simultaneous distillative removal of the resulting products.

In the lower separating zone 6 with the internals 20, the high-boiling reaction product is removed substantially from low-boiling components. In the upper separating zone 5 with the internals 22, low-boiling secondary components are substantially removed from high-boiling components. In the event of optimal column configuration, all of the cis-2-pentenenitrile may thus be converted without additional reactor and all of the trans-3-pentenenitrile obtained in the bottom without additional separating apparatus.

The catalyst packing of the distillation column in the reaction zone 21 consists of loose catalyst particles which are inserted and distributed under the action of gravity and, if required, can be discharged again. The catalyst packing has two different subregions, the catalyst particles being loosely inserted under the action of gravity and distributed in the first subregion of the packing, and, if required, being able to be discharged again, but, in the second subregion, no catalyst particles being insertable in the second subregion owing to the geometric conditions in comparison to the catalyst particles.

To increase the residence time of the reaction zone, it is possible to pass a substream through one or more side draws 29 out of the distillation column 4 through the vessel or vessels 26 and to recycle the substreams 25 leaving these vessels back into the distillation column 4 with the aid of in each case one pump 27. The vessels are filled with heterogeneous catalysts. In addition, there is heating of the vessels 26. Additionally, further cis-2-pentenenitrile-containing feed 24 may be fed into one or more vessels 26.

In the separating zones 5, 6 are disposed column internals 20, 22 having a high number of separating stages.

Heat is supplied to the reaction system and, if appropriate, in the vessel or in the vessels 26 not only via the evaporator 18, but also additionally via external heat exchangers 28 or via heat exchangers disposed directly on the column internals 20, 21 and/or 22. In addition, it is possible to draw off substreams via side draws at any point in the column. For example, it is possible to operate the column under total reflux and discharge intermediate boilers in the boiling range between cis-2-pentenenitrile and trans-3-pentenenitrile via a side draw below the catalyst packing but above the feed 3. The feed 3 is preferably within or below the separating zone 6.

The present invention is illustrated in detail with reference to the following examples:

WORKING EXAMPLES

Example 1

Heterogeneously Catalyzed Isomerization of cis-2-pentenenitrile

A. Description of the Apparatus

The experimental apparatus consists of a heatable stainless steel 2-liter reaction flask equipped with stirrer, and to which a distillation column (length: 1.2 m, diameter: 35 mm) is attached. The lower region of the column (separating zone 20) is charged with 7 segments of a structured fabric packing of the Montz A3-500 type (total height: 35 cm) and a lower region (separating zone 22) with one segment of a structured fabric packing of the Montz A3-500 type (total height: 5 cm). The reaction zone 21 in the middle region of the column was equipped with catalyst packings into which the catalyst particles are loosely inserted under the action of gravity, distributed and discharged again, the catalyst packing having first and second subregions, and the catalyst particles being loosely inserted in the first subregion of the packing under the action of gravity, distributed and discharged again, but no catalyst particles being insertable in the second subregion owing to the geometric circumstances in comparison to the catalyst particles. Overall, approx. 800 g of the catalyst are charged into the packing. Extrudates of $Al_2O_3$ are used as the catalyst. The column is equipped at regular intervals with thermoelements, so that, except in the bottom and at the top of the column, the temperature can be measured at every 3rd to 4th theoretical plate. In addition to the temperature profile, the concentration profile in the column can be determined with the aid of corresponding sampling points.

The reactants are metered into the column under mass flow control from reservoir vessels resting on balances using a pump. The evaporator 18 which is heated to 177° C. with the aid of a thermostat has a holdup of between 50 and 150 ml depending on the residence time during operation. The bottom stream 17 is conveyed from the evaporator using a pump under level control into a vessel resting on a balance. The top stream of the column 7 is condensed in a condenser (8) which is operated using a cryostat, and introduced fully 12 as reflux to the column. The apparatus is equipped with a pressure regulator 11 and designed for system pressure of 20 bar. All streams entering and leaving during the entire experiment are continuously captured and registered using a PCS. The apparatus is run in 24 hour operation (steady state).

B. Experimental Procedure

Directly above the catalyst packing, 100 g/h of cis-2-pentenenitrile (97.6% by weight, remainder other C5 nitrites) are metered continuously into the column. Extrudates of $Al_2O_3$ are used as a catalyst in the reaction zone 21. A system pressure of 1 bar and a reflux ratio, based on the feed, of 10 kg/kg, are established. The bottom temperature is 149° C. The bottom stream of the column which is drawn off is 100 g/h of product having 4.3% by weight of cis-3-pentenenitrile, 50.8% by weight of trans-2-pentenenitrile, 32.3% by weight of trans-3-pentenenitrile and 10.9% by weight of cis-3-pentenenitrile, and also other secondary components (high boilers). In total, 95.6% of the cis-2-pentenenitrile used is converted.

Example 2

Heterogeneously Catalyzed Isomerization of cis-2-pentenenitrile in a Mixture with trans-3-pentenenitrile A. Description of the Apparatus See example 1.

B. Experimental Procedure

Below the catalyst packing, 100 g/h of a mixture of trans-3-pentenenitrile (47.5% by weight) and cis-3-pentenenitrile (47.2% by weight) and also other substances from the preparation of adiponitrile by means of hydrocyanation of 1,3-butadiene are metered continuously into the column. Extrudates of $Al_2O_3$ are used as a catalyst in the reaction zone 21. A system pressure of 1 bar and a reflux ratio, based on the feed, of 10 kg/kg are established. The bottom temperature is 149° C. The bottom stream of the column which is drawn off is 100 g/h of product having 4.9% by weight of cis-2-pentenenitrile, 20.1% by weight of trans-2-pentenenitrile, 62.3% by weight of trans-3-pentenenitrile and 6.6% by weight of cis-3-pentenenitrile, and also other secondary components and high boilers. In total, 89.7% of the cis-2-pentenenitrile used is converted.

What is claimed is:

1. A process for isomerizing pentenenitrile in a reaction stream, wherein the isomerization takes place over at least one heterogeneous catalyst, selected from the group of the oxides of main group 3 or 4 or of the oxides of transition group 3 or 4 of the Periodic Table of the Elements, in a distillation column at least comprising a bottom zone, a reaction zone and a top zone, and, during the isomerization, the isomerization reactant is distillatively enriched in the reaction zone of the distillation column in relation to the isomerization product.

2. The process according to claim 1, wherein cis-2-pentenenitrile is isomerized to trans-3-pentenenitrile.

3. The process according to claim 2, wherein the trans-3-pentenenitrile is obtained in the bottom of the distillation column and the cis-2-pentenenitrile in the top of the distillation column.

4. The process according to claim 1, wherein the heterogeneous catalyst used is alumina.

5. The process according to claim 1, wherein the heterogeneous catalyst used is alumina which comprises silicon dioxide, titanium dioxide, iron dioxide, alkali metal oxides, alkaline earth metal oxides, rare earth oxides or mixtures thereof.

6. The process according to claim 1, wherein the heterogeneous catalyst is introduced into a structured packing which forms interstices in the column interior, the quotient of the hydraulic diameter for the gas stream through the structured packing or random packing and the equivalent diameter of the catalyst particles being from 2 to 20, so that the catalyst particles can be loosely inserted into the interstices under the action of gravity, distributed and discharged again if required, and the structured packing forms other interstices in which the quotient of the hydraulic diameter for the gas stream through the structured packing or the random packing and the equivalent diameter of the catalyst particles is less than 1, so that no catalyst particles can be inserted into the second subregions.

7. The process according to claim 1, wherein the isomerization is additionally carried out in the presence of a homogeneous catalyst.

8. The process according to claim 7, wherein the reaction is carried out in the presence of an ionic liquid as a homogeneous catalyst, the ionic liquid being selected from the group consisting of Brønsted acid adducts of organic nitrogen-containing substances.

9. The process according to claim 7, wherein the catalyst used is a C1- to C20-mono- or -diamine.

10. The process according to claim 1, wherein the reactant stream comprises further components selected from the group consisting of C5-mononitriles, C6-dinitriles, aliphatic C1- to C16-alkanes, cyclic C1- to C16-alkanes, aliphatic C1- to C16-alkenes, cyclic C1- to C16-alkenes.

11. The process according to claim 1, wherein the reactant stream stems from a process for hydrocyanating 3-pentenenitrile.

12. The process according to claim 1, wherein the temperature in the bottom zone of the distillation column is from 30° C. to 300° C.

* * * * *